United States Patent
Hasler et al.

(10) Patent No.: US 9,163,225 B2
(45) Date of Patent: Oct. 20, 2015

(54) METHODS FOR PURIFYING INSECT MEMBRANE-BOUND RECEPTOR PROTEINS FROM RECOMBINANT PRODUCTION HOSTS

(71) Applicant: Dow AgroSciences LLC, Indianapolis, IN (US)

(72) Inventors: James M. Hasler, Danville, IN (US); Jianquan Li, Cary, NC (US); Joel J. Sheets, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/141,890

(22) Filed: Dec. 27, 2013

(65) Prior Publication Data

US 2014/0187758 A1    Jul. 3, 2014

Related U.S. Application Data

(60) Provisional application No. 61/746,641, filed on Dec. 28, 2012.

(51) Int. Cl.
*C12N 9/48* (2006.01)
*C07K 14/435* (2006.01)

(52) U.S. Cl.
CPC .......... *C12N 9/485* (2013.01); *C07K 14/43563* (2013.01); *C07K 2319/21* (2013.01)

(58) Field of Classification Search
CPC ............. C12N 9/485; C07K 14/43563; C07K 2319/21
See application file for complete search history.

(56) References Cited

PUBLICATIONS

Kaur, Ravinder, Neema Agrawal, and Raj Bhatnagar. "Purification and Characterization of Aminopeptidase N from *Spodoptera litura* expressed in Sf21 insect cells." *Protein Expression and Purification*, 2007, 54: 267-274.

Kiefer, Hans, et al. "Expression of an Olfactory receptor in *Escherichia coli*: Purification, Reconstitution, and Ligand binding." *Biochemistry*, 1996, 35: 16077-16084.

Hobb, Rhonda I., et al. "Evaluation of Procedures for Outer Membrane Isolation from *Campylobacter jejuni*." *Microbiology*, 2009, 155: 979-988.

Bouhss, Ahmed, et al. "Purification and Characterization of the Bacterial MraY Translocase Catalyzing the First Membrane Step of Peptidoglycan Biosynthesis." *Journal of Biological Chemistry*, 2004, 279: 29974-29980.

*Primary Examiner* — Ruixiang Li
(74) *Attorney, Agent, or Firm* — Ronald S. Maciak; Barnes & Thornburg LLP

(57) ABSTRACT

The invention is drawn to a method for purifying membrane-bound proteins expressed in recombinant insect cells using N-laurosarcosine. The invention is particularly suited for expressing cadherin-type receptors cloned from *Ostrinia nubilalis*, European Corn Borer, and expressed in Sf9 insect cells. The method is optionally adapted for use with 6-his tag proteins.

**7 Claims, 3 Dr

Figure 1:
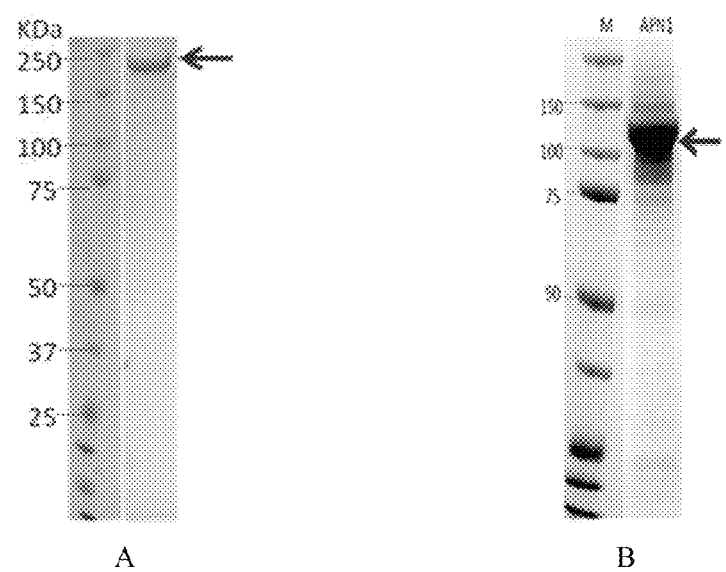
Figure 2:
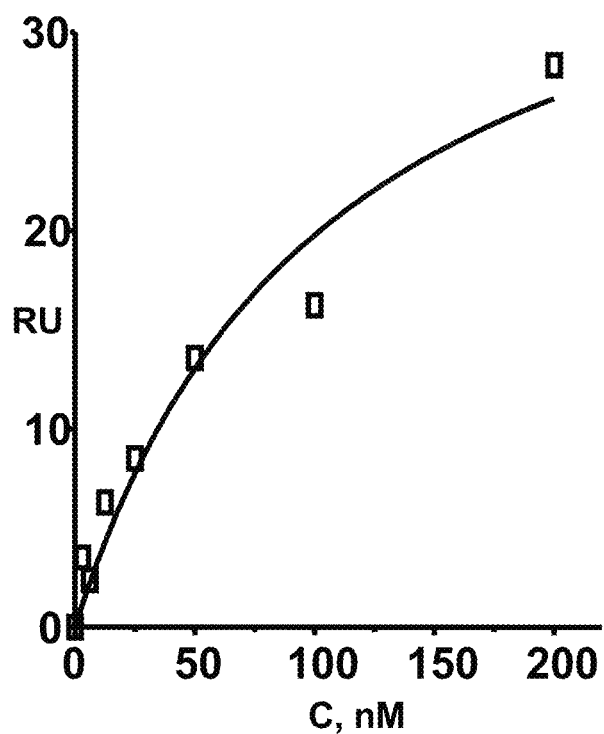
Figure 3:
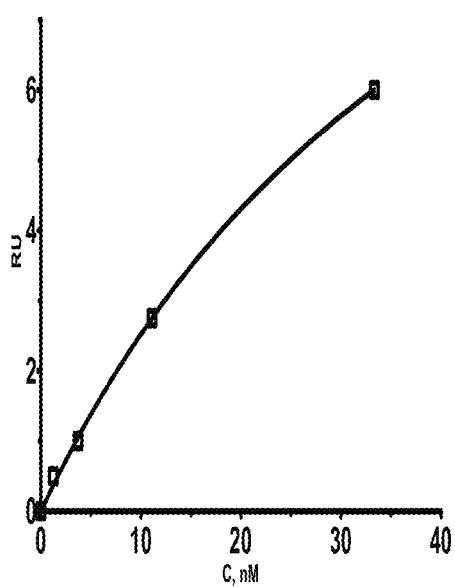

METHODS FOR PURIFYING INSECT MEMBRANE-BOUND RECEPTOR PROTEINS FROM RECOMBINANT PRODUCTION HOSTS

CROSS-REFERENCE TO RELATED APPLICATIONS

This application claims the benefit of priority under 35 U.S.C. §119(e) to U.S. Provisional Application Ser. No. 61/746,641, filed Dec. 28, 2012, the disclosure of which is incorporated herein by reference.

TECHNICAL FIELD

This invention is in the field of biochemistry and molecular biology. In particular the invention relates to purification of membrane receptor proteins from recombinant host systems.

BACKGROUND

Membrane receptor proteins located in epithelial cells of insect midguts are target sites for the action of crystalline protein toxins (cry toxins) produced by *Bacillus thuringiensis* (Bt). Activated cry toxins bind to insect receptor proteins on insect midgut epithelial cells and cause toxicity and death to specific insect pests. The specific interactions between the receptor and toxin are key events in discerning the structure-activity relationships and modes of action of these cry toxins. Being able to measure such interactions is greatly facilitated by the recombinant over production and purification of these receptor proteins to produce sufficient quantities and to reduce the level of non-specific interactions from host impurities. Using purified, functional receptor proteins in biochemical studies allows the measurement of binding affinities and specificities of the receptors in interactions with a range of Bt toxins. However, the membrane receptor proteins are typically hydrophobic, and thus are not soluble in common buffers that are suitable for most protein extractions. A specific purification protocol is described here that maximizes the solubility of hydrophobic insect membrane-bound proteins while preserving their function as receptors to toxins.

There are many reports of purifying membrane-bound proteins from recombinant hosts using N-laurylsarcosine (N-Dodecyl-N-methylglycine). See, for example, references [1-4]. However, none describes the use of a 1.0% to 0.1% gradient which the inventors found to be surprisingly effective at maximizing the solubility and activity of some hydrophobic membrane-bound receptors found in insect intestinal cell that are produced in recombinant *Spodoptera frugiperda* (Fall Armyworm) Sf9 insect cells. This method maximally solubilizes membrane receptor proteins for high yield, promotes column binding, and blocks protease cleavage. The purified receptors through this method have high purity and have retained biochemical and biological activity.

BRIEF SUMMARY OF THE INVENTION

A method for purifying a membrane-bound protein from a recombinant insect cell which comprises, suspending the recombinant insect cells in a suitable lysis buffer containing N-laurylsarcosine for an effective period of time, and optionally sonicating, centrifuging the lysate, dialyzing the supernatant against a suitable buffer containing 0.15% N-laurylsarcosine, and isolating the membrane-bound protein using one or more suitable chromatographic methods.

BRIEF DESCRIPTION OF THE DRAWINGS

FIG. 1(A) is an SDS-PAGE of purified European Corn Borer-cadherin (ECB-cadherin) and (B) European Corn Borer-aminopeptidase 1 (ECB-APN1) produced in Sf9 and purified using the claimed methods. SDS-PAGE of purified membrane receptor proteins shows more than 90% purity (See the arrows, FIGS. 1A & B). These purified receptor proteins were immobilized onto a Biacore CM4 Sensor® chip and a Cry1Ac core toxin trypsin-cleaved Cry1Ac holo-toxin) was flowed over the immobilized receptor proteins. The binding interaction was measured with a Biacore® 3000 surface plasmon resonance instrument. The binding curves are shown in FIGS. 2 and 3. The dissociation constant Kd for Cry1Ac binding to the APN-1 purified from ECB larvae was 107 nM, and that for the cadherin protein from ECB larvae was 48 nM. These values are similar to those reported in the literature [8]

FIG. 2 is a binding curve of Cry1Ac core toxin with ECB-APN1.

FIG. 3 is a binding curve of Cry1Ac core toxin with ECB-cadherin.

DETAILED DESCRIPTION OF THE INVENTION

*Ostrinia nubilalis*, European Corn Borer (ECB), is a well known pest of *Zea mays*, and Cry toxins, in a variety of forms, have been used for decades to combat this pest. It is well within the ordinarily skilled artisan's purview to introduce and express foreign genes in Sf9 insect cells. See, for example, references [5] and [6]. DNA sequences encoding ECB-cadherins have been described [7] that includes the aminopeptidase 1.

This novel method is exemplified by purifying two different membrane receptor proteins; a protein of the cadherin family, and an aminopeptidase, both from the midgut of *Ostrinia nubilalis*, that were expressed in Sf9 cells. The receptor proteins were purified to greater than 90% as judged by SDS-PAGE, and their activity was retained as confirmed by measuring their enzymatic activity in functional assays and their ability to bind Bt toxins. The binding affinity of the core Cry1Ac type Bt toxin was measured using surface plasmon resonance spectroscopy and the obtained dissociation constant are determined to be in the specific binding range as stated in the literature.

EXAMPLES

Using routine methods, Sf9 insect cells were transformed to express either ECB cadherin or ECB APN1, with or without a 6-his tag. After the cells were transformed and selected for transgenic expression, they were grown, harvested, and then frozen. Frozen Sf9 cells expressing the membrane receptors were resuspended in 50 mM CAPS or Tris (pH10.5 or 8.0), 300 mM NaCl, 1.0% (w/v) N-lauroylsarcosine, 0.1 mM DTT, and 1.0 mM PMSF. After 30 minutes incubation on ice, they were lysed with sonication, then ultra-centrifuged for one hour at 30,000 rpm (~105,000 g). The supernatant was dialysed three hours against 25 mM Tris, pH8.0, 50 mM NaCl, 0.15% (w/v) N-lauroylsarcosine, 1 mM PMSF, at the volume ratio (supernatant:buffer) of 1:2 and slow stiffing. The buffer was changed at the ratio of 1:10 for another three hours dialysis with the same slow stirring. For proteins tagged with 6-his, 10 mM imidazole was added to the dialysate, and loaded on 5 ml HisTrap HP® column (Sigma-Aldrich) pre-charged with nickel and pre-equilibrated with 25 mM Tris, pH8.0, 0.15M NaCl, 0.15% N-lauroylsarcosine. The column was washed with 50 ml washing buffer (25 mM Tris, pH8.0, 0.15M NaCl, 0.15% N-lauroylsarcosine, 10 mM imidazole). The bound proteins were eluted with elution buffer (25 mM Tris, pH8.0, 0.15M NaCl, 0.15% N-lauroylsarcosine, 0.5M imidazole). For proteins not labeled with 6-his, the dialysate was loaded on a 5 ml-HiTrap Q® column (Sigma-Aldrich) pre-equilibrated with loading buffer (20 mM Tris, pH8.0, 50 mM NaCl, 0.15% N-lauroylsarcosine, 0.5 mM EDTA, 1 mM PMSF). The column was washed with 50 ml washing buffer (20 mM Tris, pH8.0, 150 mM NaCl, 0.15% N-lauroylsarcosine, 0.5 mM EDTA, 1 mM PMSF). The protein was eluted with linear gradient: NaCl from 150 mM to 725 mM in 20 mM Tris, pH8.0, 0.15% N-lauroylsarcosine, 0.5 mM EDTA, 1 mM PMSF. For increased purity, the protein containing fractions were concentrated and further separated with a Superose® 6 10/30 column (Amersham Biosciences). The running buffer was 20 mM Tris, pH8.0, 150 mM NaCl, 0.15% N-lauroylsarcosine, 0.5 mM EDTA, 1 mM DTT.

REFERENCES

[1] Kaur et al., "Purification and Characterization of Aminopeptidase N from *Spodoptere litura* Expressed in Sf21 Insect Cells" *Protein Expression and Purification*, 54 (2007) 267-274.

[2] Kiefer et al., "Expression of Olfactory Receptors in *E. coli*; Purification, Reconstitution, and Ligand Binding" *Biochemistry* (1996) 35, 16077-16084.

[3] Hobb et al., "Evaluation of Procedures for outer membrane isolation from *Campylobacter jejuni*" *Microbiology* (2009) 155, 3, 979-988.

[4] Bouhss et al., "Purification and Characterization of the Bacterial MraY Translocase Catalyzing the First Membrane Step of Peptidoglycan Biosynthesis" *J. Biol. Chem.* (2004) 279, 29974-29980.

[5] Vaughn J L, Goodwin R H, Tompkins G J, McCawley P (1977). "The establishment of two cell lines from the insect *Spodoptera frugiperda* (Lepidoptera; Noctuidae)". *In Vitro* 13 (4): 213-217.

[6] Invitrogen (Mar. 8, 2010). "Cell Lines" (PDF). *Growth and Maintenance of Insect cell lines*. Rev. Date—8 Mar. 2010. Invitrogen. Manual part no. 25-0127, MAN0000030. (http://tools.invitrogen.com/content/sfs/manuals/insect_man.pdf.).

[7] Khajuria et al., "Expressed sequence tags from larval gut of the European corn borer (*Ostrinia nubilalis*): Exploring candidate genes potentially involved in *Bacillus thuringiensis* toxicity and resistance" (2009) *BMC Genomics* 10:286.

[8] Jenkins J L, Dean D H., "Binding specificity of *Bacillus thuringiensis* Cry1Aa for purified, native *Bombyx mori* minopeptidase N and cadherin-like receptors", *BMC Biochem.* (2001); 2:12.

What is claimed is:

1. A method for purifying a membrane-bound protein from a recombinant insect cell, said method comprising the steps of:
   a) suspending the recombinant insect cells in a lysis buffer containing N-laurylsarcosine for an effective period of time, and optionally sonicating, wherein the lysis buffer comprises 50 mM CAPS at a pH of about 10.5, 300 mM NaCl, 0.1 mM dithiothreitol, 1.0 mM PMSF, and 1.0% N-laurylsarcosine;
   b) centrifuging the lysate from step a);
   c) dialyzing the supernatant from step b) against a dialysis buffer comprising 25 mM Tris® at a pH of about 8.0, 50 mM NaCl, 1 mM PMSF, and 0.15% N-laurylsarcosine, and;
   d) isolating the membrane-bound protein using a chromatographic method.

2. The method of claim 1, wherein the recombinant insect cell is the Sf9 insect cell line.

3. The method of claim 1, wherein the isolation is performed over a HiTrap® Q column or a HisTrap HP column.

4. The method of claim 1, wherein the membrane-bound protein is a protein of the cadherin family.

5. The method of claim 1, wherein the membrane-bound protein is an aminopeptidase.

6. The method of claim 2, wherein the membrane-bound protein is a protein of the cadherin family.

7. The method of claim 2, wherein the membrane-bound protein is an aminopeptidase.

* * * * *